United States Patent [19]

Reinert et al.

[11] 3,968,298

[45] July 6, 1976

[54] PROCESS FOR IMPARTING TO NATURAL KERATIN-CONTAINING MATERIAL A PERMANENT FINISH RENDERING THE MATERIAL RESISTANT TO DAMAGE BY INSECTS

[75] Inventors: Gerhard Reinert, Allschwil; Alois Kleemann, Basel, both of Switzerland

[73] Assignee: Ciba-Geigy Corporation, Ardsley, N.Y.

[22] Filed: Aug. 4, 1972

[21] Appl. No.: 278,081

[30] Foreign Application Priority Data

Aug. 19, 1971 Switzerland.................. 12143/71

[52] U.S. Cl............................... 428/270; 424/315; 424/322; 427/421; 427/430; 428/474
[51] Int. Cl.²................. A61L 13/00; D06M 13/40
[58] Field of Search............... 117/138.5; 424/315, 424/322; 428/270; 427/421, 430

[56] References Cited

UNITED STATES PATENTS

| | | | |
|---|---|---|---|
| 2,134,001 | 10/1938 | Mills et al. | 117/138.5 |
| 2,298,681 | 10/1942 | Coleman | 117/138.5 X |
| 2,307,775 | 1/1943 | Flenner et al. | 117/138.5 X |
| 2,328,159 | 8/1943 | Martin et al. | 117/138.5 X |
| 2,363,074 | 11/1944 | Martin et al. | 424/315 X |
| 2,375,095 | 5/1945 | Flett | 424/315 |
| 2,409,883 | 10/1946 | Migrdichian | 424/316 |
| 2,469,317 | 5/1949 | Shokal et al. | 117/138.5 X |
| 2,523,114 | 9/1950 | Hawley | 117/138.5 X |
| 2,649,476 | 8/1953 | Martin | 117/138.5 X |
| 2,722,544 | 11/1955 | Martin | 117/138.5 X |

FOREIGN PATENTS OR APPLICATIONS

| | | | |
|---|---|---|---|
| 668,728 | 8/1963 | Canada | 117/138.5 |
| 1,119,189 | 4/1956 | France | |
| 703,191 | 3/1941 | Germany | |
| 946,102 | 7/1956 | Germany | |
| 488,138 | 12/1929 | Germany | |
| 200,897 | 1/1939 | Switzerland | |
| 410,519 | 10/1966 | Switzerland | |

*Primary Examiner*—Herbert B. Guynn
*Attorney, Agent, or Firm*—Joseph G. Kolodny; Edward McC. Roberts; Prabodh I. Almaula

[57] ABSTRACT

Process for the imparting of a permanent insectproof finish to natural keratin-containing material, the said process comprising the finishing of these materials in a solution of at least one salt of an anti-insect agent protecting against keratin-consuming insects, said salt consisting of the anionic radical of an insecticide and an inorganic and/or organic cation capable of salt formation, and, optionally, further additives, in a solvent mixture consisting of a. 66 to 99 per cent by weight of an optionally halogenated hydrocarbon boiling between 40° and 150°C, and b. 40 to 1 per cent by weight of a liquid, water-soluble organic solvent boiling below 220°C, as well as the treatment liquor suitable for and the material permanently finished by this process.

14 Claims, No Drawings

PROCESS FOR IMPARTING TO NATURAL KERATIN-CONTAINING MATERIAL A PERMANENT FINISH RENDERING THE MATERIAL RESISTANT TO DAMAGE BY INSECTS

The present invention relates to a process for imparting to natural keratin-containing material a permanent finish rendering the material resistant to damage by insects, said finish being applied from a solvent mixture containing salts of agents protecting against insects (anti-insect agents); to the treatment liquor suitable for this process; and to the material, as an industrial product, permanently finished by this process.

Year by year insects, such as wool pests, are responsible for the destruction of wool textile material to the value of many millions of dollars. Methods of protecting wool textiles and keratin-fibre-containing textiles from damage caused by keratin-consuming insects are known; e.g., by destruction of the insects by means of control agents acting as poisons (insecticides), or with the aid of contact or stomach poisons, such effects being achieved by the preparation of the textile materials with the required agents, or by application, in a manner similar to that for dyestuffs, of stomach poisons to the fibres from an aqueous bath.

The hitherto best process, both technically and economically, for the protection of wool from keratin-consuming insects consists in the application of moth-proofing agents which have affinity to wool, which can be fixed on the fibres, and which can be applied during the dyeing and finishing of wool textiles. These moth-proofing agents behave like wool dyestuffs in their application and are therefore often described as 'colourless dyestuffs'. The disadvantage is, however, that by this process the application of moth-proofing agents has hitherto been possible only from aqueous solutions or dispersions. Since it is commonly known, however, that wool fibres are particularly sensitive to water, in that, for example, they become matted or shrink, processes have been sought which would enable these disadvantages to be eliminated. It is further known that certain moth-proofing agents can be applied from pure organic solvent. Materials having a moth-proof finish are thus obtained, but the resulting finish is fast neither to washing nor to dry cleaning.

It has now been found that the afore-mentioned disadvantages are overcome when the anti-insect finish is imparted to natural keratin-containing materials by treating them in organic solvent mixtures.

By virtue of this 'solvent'-process, the anti-insect agent remains, after being fixed on the material, permanently fast to washing and to solvents. Furthermore, there occurs no matting or shrinking of the material.

The process according to the invention comprises imparting to the materials a permanent anti-insect finish, said finish being obtained by treatment of the materials in a solution of at least one salt of an anti-insect agent protecting against keratin-consuming insects, the salt consisting of the anionic radical of an insecticide and an inorganic and/or organic cation capable of salt-formation, and, optionally, further auxiliaries, in a solvent mixture consisting of a. 60 to 99 per cent by weight of an optionally halogenated hydrocarbon boiling between 40° and 150°C, and
b. 40 to 1 per cent by weight of a liquid, water-soluble organic solvent boiling below 220°C.

The term 'permanent' is to indicate that the anti-insect finish is retained even after repeated chemical cleaning, either in an aqueous or in a solvent washing medium.

Suitable optionally halogenated hydrocarbons boiling between 40° and 150°C suitable as constituent a) of the solvent mixture are, e.g. aromatic or aliphatic hydrocarbons such as benzene, toluene, xylene or petroleum fractions (heavy gasoline); preferably, however, halogenated, especially chlorinated, hydrocarbons such as mono- and dichlorobenzene, and particularly, because of their generally greater ease of regeneration and noncombustibility, lower aliphatic halogenated hydrocarbons such as chlorinated hydrocarbons, e.g. chloroform, carbon tetrachloride, trichloroethylene, tetrachloroethylene ("perchloroethylene"), tetrachloroethane, 1,1,1-trichloroethane or dibromoethylene, as well as mixed halogenated hydrocarbons, e.g. 1,1,2-trichloro-2,2,1-trifluoroethane. Mixtures of such solvents may also be used.

By liquid, water-soluble organic solvents boiling below 220°C, which are suitable as constituent b) of the solvent mixture, are meant thermostable solvents which are soluble in water not only to the extent of fractions of one per cent but also to the extent of several per cent. Examples of such solvents are: higher alkanols such as butanols or amyl alcohols; cycloaliphatic alcohols such as cyclohexanol; araliphatic alcohols such as benzyl alcohol; aliphatic or cycloaliphatic ketones such as methyl ethyl ketone and cyclohexanone.

Preferred solvents according to b) are, however, solvents miscible with water in any proportion. Examples of these are: monovalent lower aliphatic alcohols such as lower alkanols, e.g. methanol, ethanol and n- or isopropanol; alkylene glycol monoalkyl ethers such as ethylene glycol monomethyl or -ethyl ethers; and also furfuryl alcohol or tetrahydrofurfuryl alcohol, or bivalent aliphatic alcohols such as ethylene glycol or 1,2-propylene glycol; also lower aliphatic ketones such as acetone, lower cyclic ethers such as dioxane; also N,N-dialkylamides of lower monocarboxylic acids such as dimethylformamide or dimethylacetamide; amides of carbonic acid such as N,N,N',N'-tetramethylurea, or tertiary organic amines such as pyridine, as well as mixtures of such liquid, water-soluble organic solvents.

Preferred solvent mixtures are those consisting of 80 to 99 per cent by weight of halogenated, particularly chlorinated, lower aliphatic hydrocarbon boiling between 40 and 150°C, especially 90 to 99 per cent by weight of trichloroethylene, 1,1,1-trichloroethane, tetrachloroethylene or trifluorotrichloroethane, and 20 to 1 per cent by weight of a liquid, water-soluble organic solvent, preferably miscible with water in any proportion and boiling below 220°C, particularly 10 to 1 per cent by weight of methanol, methylcellosolve or dimethylformamide.

The composition of the solvent mixture is governed by the solubility of the anti-insect agent to be used, and should be of such a nature that a homogeneous and clear solution is obtained.

The salt of the anti-insect agent consists of the anionic radical of an insecticide and an inorganic and/or organic cation. The cattions are, in particular, inorganic cations such as alkali metal cations, e.g. sodium or ammonium ions; or organic cations, e.g. an organic nitrogen compound having a nitrogen atom, capable of salt formation, which can be in the form of a primary, secondary, tertiary amino group or quaternary ammonium group. In the case of organic cations the following organic compounds may be mentioned as being particularly suitable for salt formation:

1. Substituted or unsubstituted aliphatic amines, particularly alkylamines such as butylamine, hexylamine, octylamine, decylamine, dodecylamine, tetradecylamine, octadecylamine, diethylamine, dibutylamine, dioctylamine, didodecylamine, N-methyl-N-dodecylamine, N-ethyl-N-octadecylamine, triethylamine, tributylamine, N,N-dimethyl-N-dodecylamine, N,N-dimethyl-N-octadecylamine, β-hydroxyethylamine, γ-hydroxypropylamine, N-β-hydroxyethyl-N-dodecylamine, γ-methoxypropylamine, N-γ-methoxypropyl-N-dodecylamine, N-β-hydroxyethyl-N-octadecylamine, N,N-dimethyl-N-benzyldodecylammonium hydroxide, N,N,N-trimethyloctadecylammonium hydroxide and trimethyldodecylammonium hydroxide.

2. Substituted or unsubstituted aliphatic di- and triamines such as 1,2-ethylenediamine, 1,3-propylenediamine, diethylenetriamine, 1,1-bis-methylpropylenediamine, 1,1-bis-dodecylpropylenediamine, 1,1-biscyclohexylpropylenediamine, 1,1-bis-benzylpropylenediamine, N,N'-bis-phenylethylenediamine, N,N,N',N'-tetrapropylpropylenediamine, N,N,N',N'-tetrabenzylpropylenediamine, N,N,N',N', -tetra-β-hydroxyethylpropylenediamine, 1-dodecyl-1-ethylenediamine, 1-octadecylethylenediamine and 1-octadecyldiethylenetriamine.

3. Substituted or unsubstituted cycloalkylamines such as cyclohexylamine, N-methylcyclohexylamine, N-octylcyclohexylamine, N-β-hydroxyethylcyclohexylamine, N-methyl-N-β-hydroxyethylcyclohexylamine, dicyclohexylamine, dehydroabietylamine and trimethylcyclohexylammonium hydroxide.

4. Substituted or unsubstituted aralkylamines such as benzylamine, β-phenylethylamine, N-β-hydroxyethylbenzylamine, N-γ-methoxypropylbenzylamine, N-β-cyanoethylbenzylamine, N-methyl-N-γ-methoxypropylbenzylamine, N-octylbenzylamine, N-octadecylbenzylamine and dibenzylamine.

5. Substituted and unsubstituted aromatic amines, especially mononuclear aromatic amines such as aniline, N-methylaniline, N,N-dimethylaniline, N,N-dibutylaniline, N-β-hydroxyethyl-N-methylaniline and toluidine.

6. Unsubstituted or substituted amidines, preferably alkylamidines such as acetamidine, benzamidine, laurylamidine, stearylamidine, as well as N-methyllaurylamidine, N-butyllaurylamidine, N-phenyllaurylamidine, N-benzyllaurylamidine, N-methylstearylamidine, N-benzylstearylamidine or N-cyclohexylstearylamidine.

7. Substituted isothioureas, preferably S-alkylisothioureas, such as S-benzylisothiourea, S-hexyl-, S-octyl-, S-undecyl, S-dodecyl, S-octadecyl and S-octadecenylisothiourea.

8. Guanidines, especially alkylguanidines, such as dodecylguanidine, octadecylguanidine and octadecenylguanidine, as well as phenylguanidine and benzylguanidine.

9. Hydrazines such as phenylhydrazine or undecylhydrazine.

10. Nitrogen-containing five- and six-membered heterocycles which can be partially or completely saturated.

Suitable five-membered, nitrogen-containing heterocycles are, e.g.: pyrrols such as methylpyrrol and benzylpyrrol; pyrrolines such as methylpyrroline or benzylprroline; also pyrrolidines such as methylpyrrolidine, butylpyrrolidine or dodecylpyrrolidine; pyrazoles; pyrazolines such as N-methylpyrazoline; pyrazolidines, particularly unsubstituted and substituted 2-alkylimidazolines such as 2-heptylimidazoline, 2-undecylimidazoline, 2-heptadecyclimidazoline, 2-heptadecenylimidazoline, 1-methyl-2-undecylimidazoline, 1-β-hydroxyethyl-2-undecylimidazoline, 1-β-hydroxyethyl-2-heptadecylimidazoline and 2-aminoethyl-1-heptadecylimidazoline.

Suitable six-membered, nitrogen-containing heterocycles are, e.g.: piperidine and its derivatives, particularly N-alkyl- or N-aralkylpiperidines such as N-methylpiperidine, N-dodecylpiperidine and N-benzylpiperidine; piperazines such as N-octadecylpiperazine; morpholine and, in particular, its N-alkyl and N-aralkyl derivatives such as N-butylmorpholine, N-octadecylmorpholine or N-benzylmorpholine; quinuclidine, pyridine, N-methylpyridinium hydroxide and octadecyloxymethylenepyridinium hydroxide; pyrimidines such as dihydro- and, in particular, tetrahydropyrimidines, preferably 2-alkyltetrahydropyrimidines such as 2-heptyltetrahydropyrimidine, 2-undecyltetrahydropyrimidine, 2-heptadecyltetrahydropyrimidine, 2-heptadecenyltetrahydropyrimidine, 1-methyl-2-undecyltetrahydropyrimidine or 1-β-hydroxyethyl-2-heptadecyltetrahydropyrimidine; 2-amino-1-octadecyltetrahydropyrimidine; 1,3,5-triazines, particularly derivatives of 2,4,6-triamino-1,3,5-triazine such as 2-dodecylamino-4,6-bis-amino-1,3,5-triazine and 2-octadecylamino-4,6-bisamino-1,3,5-triazine, 2-heptadecyl-4,6-bis-amino-1,3,5-triazine; or hexahydro-1,3,5-triazine derivatives.

11. Condensed nitrogen-containing heterocycles such as indolines and indoles.

The following are preferred: alkylamines having an alkyl radical preferably containing 12 to 18 carbon atoms, especially dodecylamine and octadecylamine; alkylguanidines having preferably 12 to 18 carbon atoms in the alkyl radical, such as dodecylguanidine or octadecylguanidine; alkylamidines preferably having 12 to 18 carbon atoms in the alkyl radical, such as N-methylstearylamidine or N-benzyllaurylamidine; 2-alkylimidazolines and 2-alkyltetrahydropyrimidines having preferably 11 to 18 carbon atoms in the alkyl radical, such as 2-undecylimidazoline, 2-heptadecylimidazoline, 2-undecyltetrahydropyrimidine as well as 2-heptadecyltetrahydropyrimidine and their 1-alkyl derivatives; cycloalkylamines and aralkylamines such as dicyclohexylamine and dibenzylamine and, preferably, S-alkylisothioureas having an alkyl radical preferably containing 11 to 18 carbon atoms, such as S-undecyl-, S-dodecyl and S-octadecylisothiourea.

Suitable insecticide salts applicable according to the invention are, in particular, compounds, containing sulphonic acid groups, of formula I

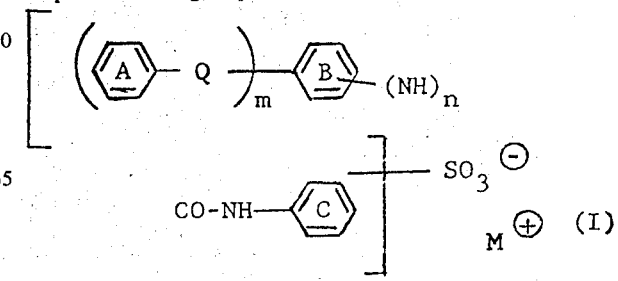

in which the benzene ring

A is substituted by one or two chlorine or bromine atoms, or by a chlorine atom and a methyl group, the benzene ring B by a chlorine or bromine atom and/or by a trifluoromethyl group, and the benzene ring C by one to three chlorine or bromine atoms, or by one to two trifluoromethyl groups, or by a chlorine atom and a trifluoromethyl group, or by a chlorine atom and a p-chlorophenoxy group, and in which Q represents the direct carbon bond or an oxygen or a sulphur bridge, m and n each independently represent 0 or 1, and M denotes an inorganic or organic cation capable of salt formation.

Of these compounds those particularly preferred, on account of their good insecticidal action against keratin-consuming insects, are the compounds of formula II

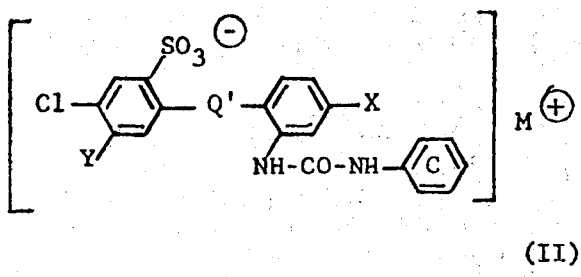

(II)

in which the benzene ring

C is substituted by one to two chlorine atoms, or by one to two trifluoromethyl groups, or by a chlorine atom and a trifluoromethyl group, and in which Q' represents the oxygen or the sulphur bridge, X represents a chlorine atom or a trifluoromethyl group, and Y represents hydrogen or a chlorine atom, and $M^+$ has the meaning defined under formula I.

The employed salts of anit-insect agents are known and can be produced by known methods.

These insecticide salts are very good stomach poisons against the larvae of the most important wool pests. These pests are, e.g.: species of moths such as the clothes moth [Tineola bisselliella], the pelt moth [Tinea pellionella], the carpet moth [Trichophaga tapetiella]; or species of carpet beetles such as the common carpet beetle [Anthrenus scrophulariae], the banded carpet beetle [Anthrenus fasciatus], the mullein flower beetle [Anthrenus verbasci], the burnet-saxifraga flower beetle [Anthrenus pimpinellae], the museum beetle [Anthrenus museorum]; or species of pelt beetle such as the common pelt beetle [Attagenus pellio] and the black pelt beetle [Attagenus piceus].

The treatment liquor to be used according to the invention contains, depending on the effectiveness of the insecticide salt employed, from 0.01 to 5, and particularly from 0.1 to 2, per cent by weight of this insecticide salt, relative to the keratin-containing material.

Particularly good finishing effects are obtained if an addition is made to the treatment liquor of an auxiliary such as a system-soluble, lower aliphatic or aromatic carboxylic acid, e.g. formic acid, acetic acid or phenylacetic acid. The preferred acid is 100% acetic acid (glacial acetic acid).

The above auxiliaries are added to the extent of ca. 0.5% to 4%, and particularly 0.5% to 2%, relative to the weight of the keratin-containing material.

Suitable keratin-containing natural materials which are finished according to the invention are, in particular, wool and other keratin-containing materials, such as hair, bristles, feathers, etc.

The finishing of these keratin-containing natural materials is preferably performed by the exhaust process, or by spraying, e.g. in drycleaning apparatus. In the latter case, the material is advantageously sprayed at room temperature, whereas the exhaust process is preferably carried out at elevated temperature, e.g. at 20° to 70°C, for 5 to 40 minutes.

The process according to the invention renders possible the application of anti-insect agents from organic solvents with extensive exhaustion of the liquors. The moth-proofing agent in the present process, unlike in hitherto known processes, is fixed in the wool, i.e. the agent is resistant to drycleaning, and hence can be applied in an economic manner, since it is not necessary to operate with excess amounts.

The said process moreover enables anti-insect agents to be economically applied from solvents at temperatures at which an application from water, or from water-in-perchloroethylene emulsions, is limited or even impossible. The fact may be emphasized, in particular, that in the solvent mixture, perchloroethylene/methanol, according to the invention there can occur, under the conditions of the process, no matting or shrinking of the wool, in contrast to that occurring in all processes with water.

The process can be performed both as a pretreatment and as an aftertreatment in relation to other processes.

There are obtained by the process according to the invention, on the defined material, finishing effects which are level and fast, e.g. fast to drycleaning.

A further advantage of the process according to the invention consists in the fact that the employed solvents can be recovered and fed back into the finishing process, the problem of effluent purification being thus eliminated. A further advantage of the new process is that the insecticide salts are stomach poisons for insects and thus, when properly applied, harmless to humans. This a particular advantage, especially where clothing is concerned.

The process according to the invention need not necessarily be performed separately; it can be carried out without any special difficulties, for example, during the dyeing process, or during some other standard finishing operation, (e.g. a finishing process for making wool shrink proof and free from matting) or even simultaneously with drycleaning.

The advantages of the process according to the invention are thus as follows:

1. application under conditions favorable to the wool; no occurrence of matting and shrinking, since the application is effected without water and emulsifier;
2. obtainment of a drycleaning-fast fixing of the anti-insect agent;
3. extensive exhaustion of the finishing baths (economic application);
4. the process may also be carried out in standard drycleaning machines;

5. since many polar solvents form with the preferred solvent, perchloroethylene, an azeotrope, the cosolvent can be recovered without difficulty;
6. the process according to the invention can be performed at room temperature;
7. the use of low application temperatures the aesthetic properties (handle, softness) of the wool to be retained to a great extent.

The invention also relates to the treatment liquor suitable for the finishing of natural keratin-containing material, the said treatment liquor containing at leastt one salt of an anti-insect agent protecting aganist keratin-consuming insects, the said salt consisting of the anionic radical of an insecticide and an inorganic and/or organic cation capable of salt formation, and, optionally, further auxiliaries, dissolved in a solvent mixture consisting of:

a. 60 to 99 per cent by weight of an optionally halogenated hydrocarbon boiling between 40° and 150°C, and
b. 40 to 1 per cent by weight of a liquid, water-soluble organic solvent boiling below 220°C.

The following non-limitative examples illustrate the invention. Temperatures are expressed in degrees centigrade and the term 'parts' denotes parts by weight.

EXAMPLE 1

An amount of 100 mg of the anti-insect agent (ca. 92.5% of active substance) of the formula

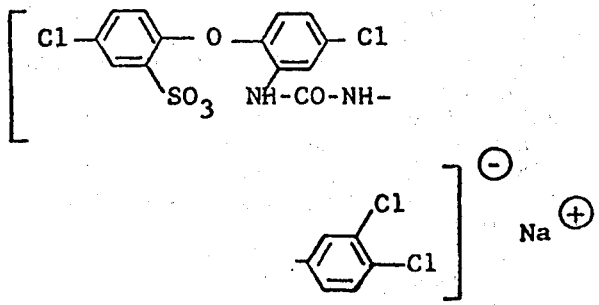

is dissolved in 1 ml of ethylene glycol monoethyl ether, and the solution then added to 75 ml of a mixture of 96 per cent by volume of perchloroethylene and 4 per cent by volume of methanol. In order to correct the pH-value of the wool, an addition corresponding to 2% of the weight of wool is made of glacial acetic acid. This solution is transferred to a vibrating apparatus and 10 g of a wool flannel fabric treated therein at 45° for 30 minutes. The fabric is afterwards centrifuged and dried with warm air.

The amount of anti-insect agent on the wool flannel fabric is analytically determined; the obtained results show a yield of 78% of the employed amounts of insecticide.

The wool fabric treated in this manner is drycleaned twice for 20 minutes at 25° with perchloroethylene, the perchloroethylene containing per litre 5 g of dry cleaning detergent and 10 g of water (ratio of goods to liquor = 1:20).

The amount of anti-insect agent on the wool flannel twice drycleaned is again analytically determined; the results show a fixed yield of 77%.

The wool flannel fabric thus treated was biologically tested. The biological findings are given in the following Table I.

Table I

|  | Moth - test | | Attagenus test | | Anthrenus test | |
| --- | --- | --- | --- | --- | --- | --- |
|  | original | twice drycleaned | original | twice drycleaned | original | twice drycleaned |
| moth- or beetle-proofing | very good | very good | good | good | very good | very good |
| surviving larvae | <2 % | <2 % | 2–4 % | 2–4 % | 2.5 % | 2.5 % |

EXAMPLE 2

6.6 Parts of an anti-insect agent containing 85.6% of active substance of the formula

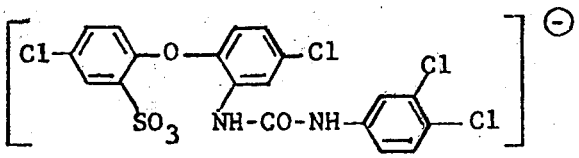

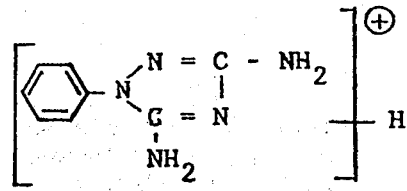

are dissolved in 100 ml of methanol, and the solution then added to a mixture of 7.2 liters of perchloroethylene, 200 ml of methanol and 10 ml of glacial acetic acid. The clear liquor is transferred to a solvent — cheese apparatus containing a 500 g cheese of a wool, carded yarn (ratio of goods to liquor 1:15). The liquor is heated for 5 minutes to 45°, and the wool carded yarn treated for 30 minutes at this temperature. Centrifuging is then carried out in the apparatus followed by drying.

The wool carded yarn treated in this manner has a 99% yield of analytically determined anti-insect agent.

The wool yarn is drycleaned twice as described in Example 1, whereupon the amount of anti-insect agent retained on the cleaned wool yarn is analytically determined at 95.4%.

The wool carded yarn thus has a finish which is insect- and beetleproof.

EXAMPLES 3 to 9

If, instead of the anti-insect agent used in Example 2, the insecticide salts listed in the following Table II, Column II, are used, the procedure being otherwise analogous to that described in Example 2, then similar yields and effects are obtained.

Table II

| Ex. No. | Insecticide salt | |
|---|---|---|
| | Anion | Cation |
| 3 | $\left[\text{Cl}-\underset{\text{SO}_3}{\bigcirc}-\text{O}-\underset{\text{NH-CO-NH}}{\bigcirc}-\text{Cl} \quad \underset{\text{Cl}}{\bigcirc}-\text{Cl}\right]^\ominus$ | $\left[C_{11}H_{23}-C\overset{N-CH_2}{\underset{NH-CH_2}{\diagdown}}\!\!\!\!\!\!+\!\!\!\!\!\!\text{H}\right]^\oplus$ |
| 4 | do | $\left[C_{17}H_{35}-C\overset{N-CH_2}{\underset{NH-CH_2}{\diagdown}}\!\!\!\!\!\!+\!\!\!\!\!\!\text{H}\right]^\oplus$ |
| 5 | do | $\left[C_{18}H_{37}-NH-\underset{NH}{\overset{\|}{C}}-NH_3\right]^\oplus$ |
| 6 | do | $\left[\langle H\rangle-NH_2-\langle H\rangle\right]^\oplus$ |
| 7 | do | $\left[C_{12}H_{25}NH_3\right]^\oplus$ |
| 8 | do | $\left[C_{18}H_{37}NH_3\right]^\oplus$ |
| 9 | do | $\left[\langle\bigcirc\rangle-CH_2-NH_3\right]^\oplus$ |

EXAMPLE 10

An amount of 100 ml of a solvent mixture is prepared consisting of 96 per cent by volume of perchloroethylene, 4 per cent by volume of methanol, and glacial acetic acid to the extent of 2 per cent by weight of the wool used. An addition is made to this solution of an amount, corresponding to 1.4% of the weight of wool, of the anti-insect agent of the formula

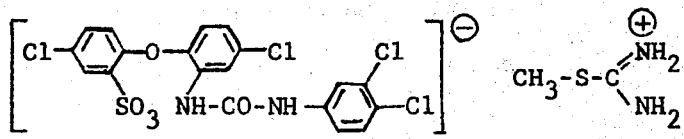 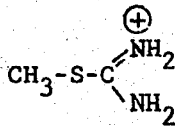

dissolved in the 10-fold amount of ethylene glycol monoethyl ether. With a ratio of goods to liquor of 1:15, 10 g of wool tricot is treated in the above solution, with continuous movement, at a temperature of 45° for 30 minutes. The fabric is afterwards centrifuged, and dried at 70°. The fabric treated in this manner has the following analytical content of anti-insect agent:

| | |
|---|---|
| finished original sample | 0.96% |
| sample after 2 drycleanings | 0.89% |

The results of the biological evaluation indicate for the original sample, and also for the sample drycleaned twice, a very good proofing against moths and anthrenus (surviving larvae < 2%), and a good proofing against attagenus larvae (surviving larvae 2.5 to 5%).

EXAMPLES 11 AND 12

Instead of the methylisothiouronium salt cation according to Example 10, it is also possible to use the following cations, with the anion unchanged:

| Example No. | Cation |
|---|---|
| 11 | $\left[ C_{18}H_{37}-S-C\begin{array}{c}\nearrow NH_2 \\ \searrow NH_2\end{array}\right]^{\oplus}$ |
| 12 | $\left[ C_6H_5-CH_2-S-C\begin{array}{c}\nearrow NH_2 \\ \searrow NH_2\end{array}\right]^{\oplus}$ |

Similarly good finishings are obtained.

EXAMPLES 13 TO 65

If, instead of the salts of the anti-insect agents according to Examples 1 to 12, salts of anions according to the following Table III, Column II, combined with the cations according to Examples 1 to 12, are used as antiinsect agents, with otherwise the same procedure as given in Examples 1 to 12, then equally good insect-proof finishings are obtained on wool flannel fabric.

Table III

| I Ex. No. | II Insecticide Anion |
|---|---|
| 13 | Cl–C$_6$H$_3$(SO$_3^{\ominus}$)–O–C$_6$H$_3$(Cl)–NH–CO–NH–C$_6$H$_3$(CF$_3$)(Cl) |
| 14 | Cl–C$_6$H$_3$(SO$_3^{\ominus}$)–O–C$_6$H$_3$(Cl)–NH–CO–NH–C$_6$H$_3$(CF$_3$)(CF$_3$) |
| 15 | Cl–C$_6$H$_3$(SO$_3^{\ominus}$)–O–C$_6$H$_3$(Cl)–NH–CO–NH–C$_6$H$_3$(Cl)(Cl) |
| 16 | Cl–C$_6$H$_3$(SO$_3^{\ominus}$)–O–C$_6$H$_3$(Cl)–NH–CO–NH–C$_6$H$_3$(Cl)–O–C$_6$H$_4$–Cl |
| 17 | Cl–C$_6$H$_4$–O–C$_6$H$_3$(Cl)–NH–CO–NH–C$_6$H$_3$(Cl)–Cl, with SO$_3^{\ominus}$ substituent |

Table III -continued
| I | II |
|---|---|
| 18 | 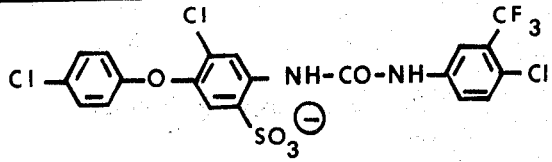 |
| 19 | 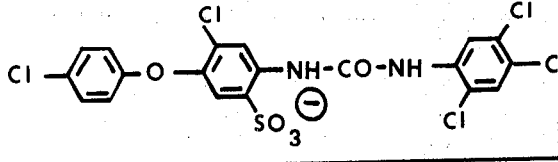 |
| 20 | 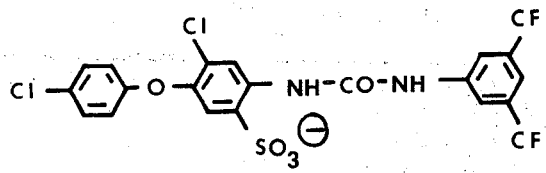 |
| 21 | 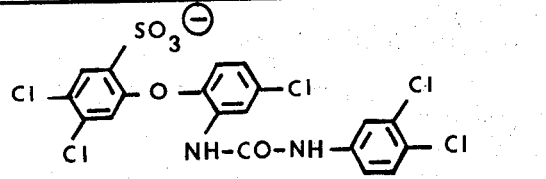 |
| 22 | 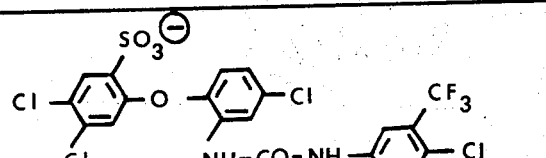 |
| 23 | 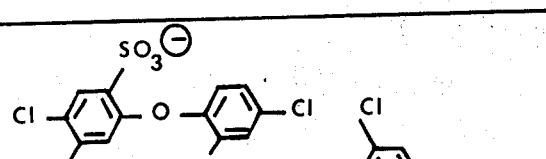 |
| 24 | 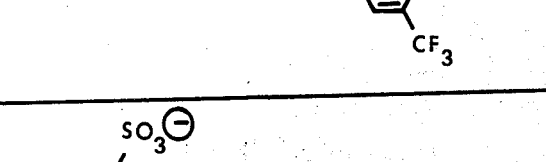 |
| 25 | 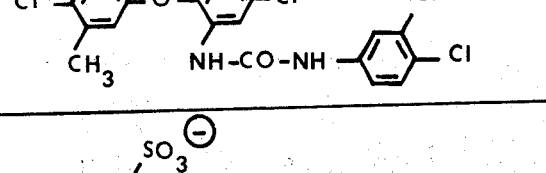 |
| 26 | 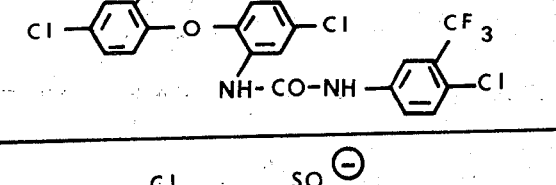 |

Table III -continued

| I | II |
|---|---|
| 27 | 2,4-dichlorophenoxy-(5-chloro-2-sulfonato)phenyl-NH-CO-NH-(3,4-dichlorophenyl) |
| 28 | (4,5-dichloro-2-sulfonato)phenyl-O-(5-trifluoromethyl-2-aminophenyl)-NH-CO-NH-(3-trifluoromethylphenyl) |
| 29 | (4,5-dichloro-2-sulfonato)phenyl-O-(4-chloro-2-aminophenyl)-NH-CO-NH-(3-trifluoromethylphenyl) |
| 30 | (4-chloro-2-sulfonato)phenyl-O-(5-trifluoromethyl-2-aminophenyl)-NH-CO-NH-(3-trifluoromethylphenyl) |
| 31 | (4-chloro-2-sulfonato)phenyl-O-(5-trifluoromethyl-2-aminophenyl)-NH-CO-NH-(3,4-dichlorophenyl) |
| 32 | (4-chloro-2-sulfonato)phenyl-O-(5-trifluoromethyl-2-aminophenyl)-NH-CO-NH-(4-chloro-3-trifluoromethylphenyl) |
| 33 | (4-chlorophenyl)-O-(3-chloro-4-aminophenyl)-NH-CO-NH-(3-trifluoromethyl-4-chloro-5-sulfonatophenyl) |
| 34 | (4-chlorophenyl)-O-(5-chloro-2-aminophenyl)-NH-CO-NH-(3,4-dichloro-6-sulfonatophenyl) |

Table III -continued
| I | II |
|---|---|
| 35 | 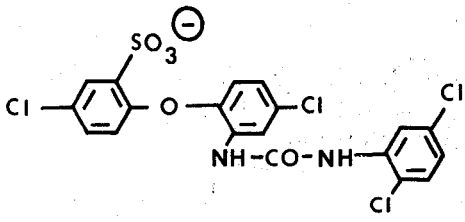 |
| 36 | 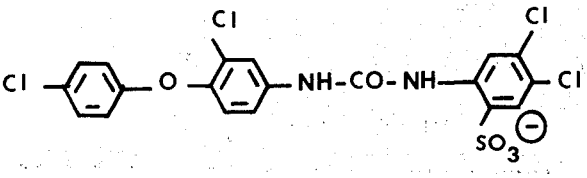 |
| 37 | 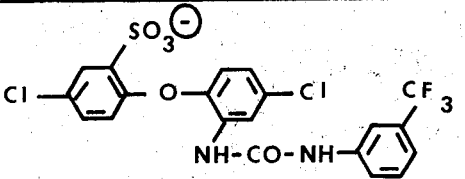 |
| 38 | 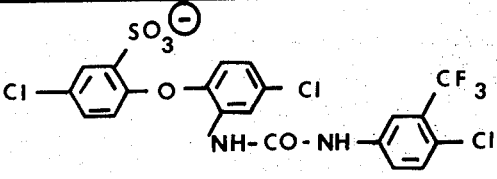 |
| 39 | 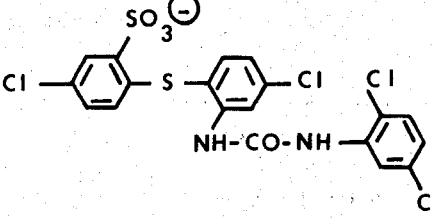 |
| 40 | 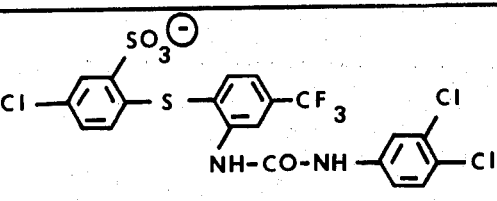 |
| 41 | 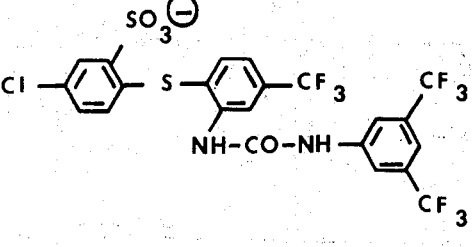 |
| 42 | 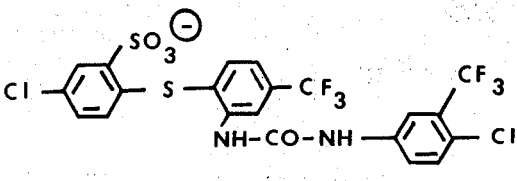 |

Table III -continued
| I | II |
|---|---|
| 43 | 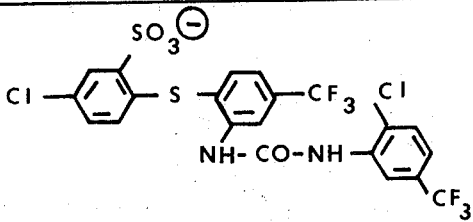 |
| 44 | 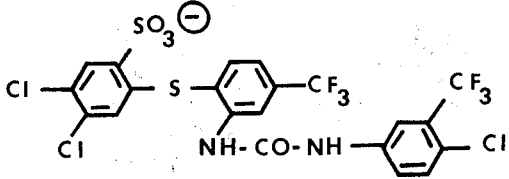 |
| 45 | 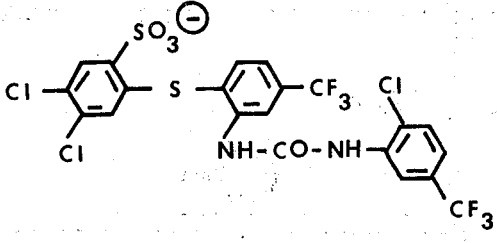 |
| 46 | 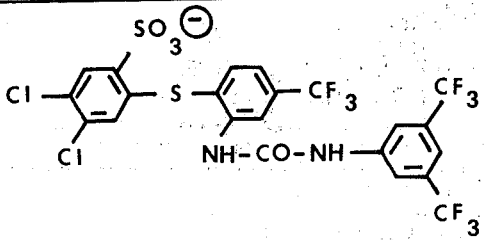 |
| 47 | 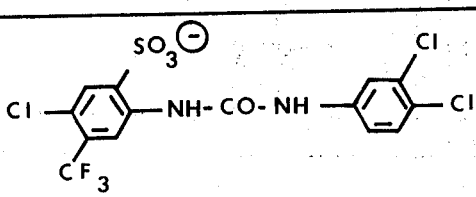 |
| 48 | 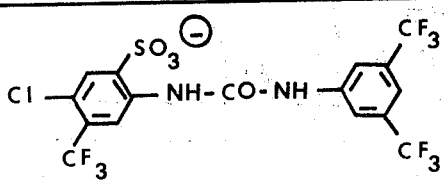 |
| 49 | 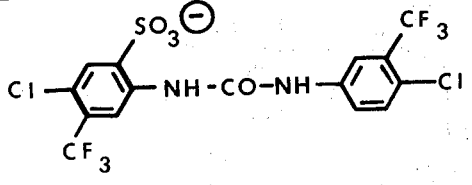 |
| 50 | 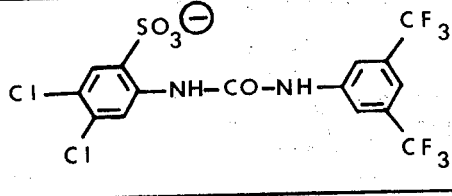 |

Table III-continued
| I | II |
|---|---|
| 51 | 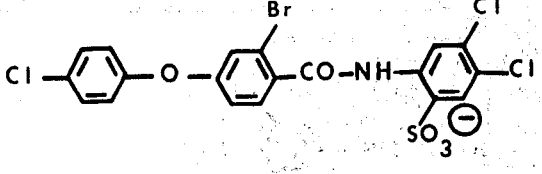 |
| 52 | 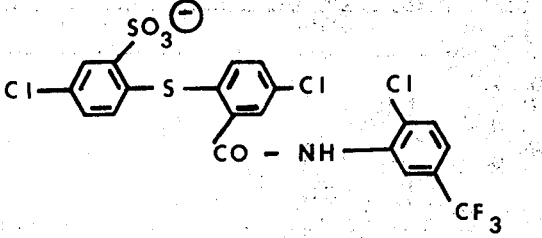 |
| 53 | 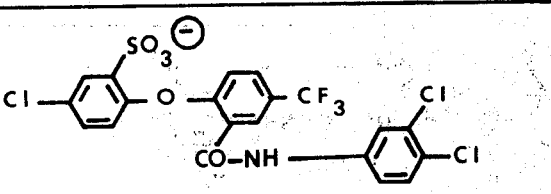 |
| 54 | 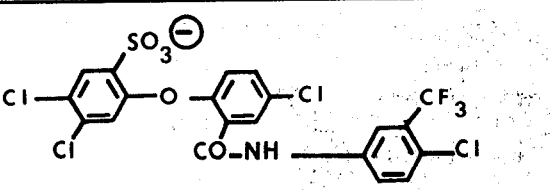 |
| 55 | 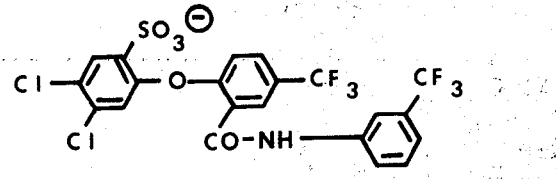 |
| 56 | 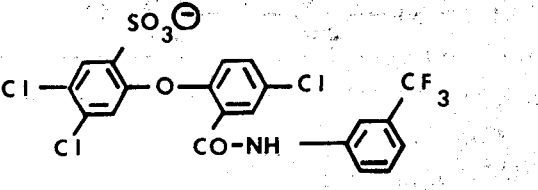 |
| 57 | 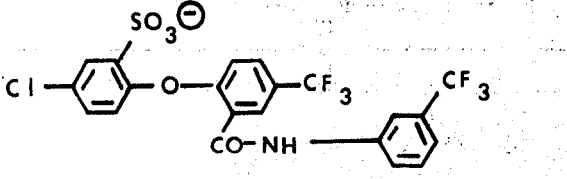 |
| 58 | 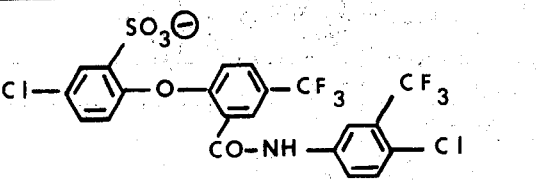 |

Table III -continued
| 1 | II |
|---|---|
| 59 | 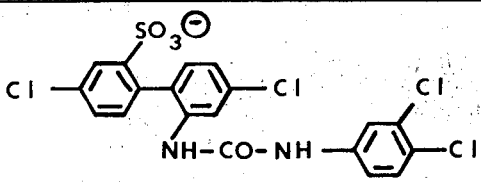 |
| 60 | 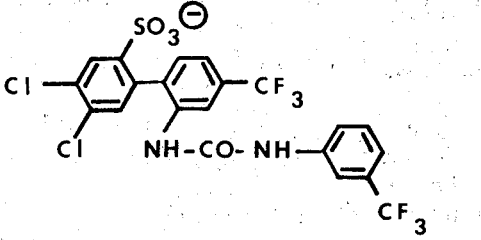 |
| 61 | 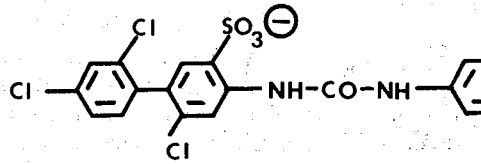 |
| 62 | 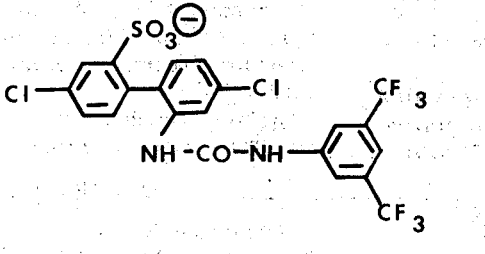 |
| 63 | 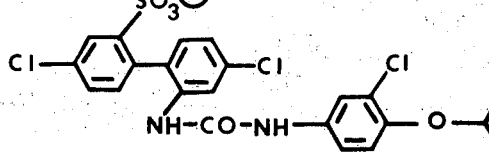 |
| 64 | 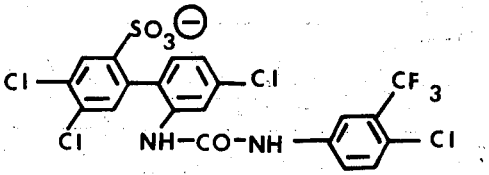 |
| 65 | 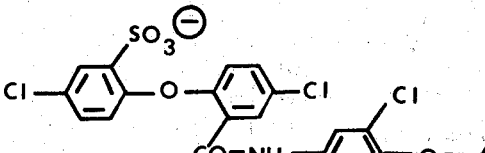 |

EXAMPLES 66 TO 71

Examples 66 to 71 illustrate the various degrees of fixing of the anti-insect agents on keratin-containing materials after application from treatment liquors of varying composition: a water-insoluble solvent only is used in Example 66, and in Examples 67 to 71 a solvent mixture of a water-soluble and a water-insoluble solvent.

EXAMPLE 66

An amount of 110 mg of the anti-insect agent described in Example 2 (1.1 per cent by weight relative to the treated material) is dissolved in 100 ml of perchloroethylene to obtain a clear solution.

A sample of 10 g of wool flannel is subsequently placed into the solvent liquor at 60°, and this textile material treated at this temperature, with continuous agitation of the liquor, for 45 minutes After being centrifuged, the wool flannel is dried at 70°, and the wool specimen then analytically (following Table IV) and biologically (following Table V) examined.

EXAMPLES 67 TO 71

In each case, 110 mg of the anti-insect agent described in Example 2 is predissolved in 1.5 ml of ethylene glycol ethyl ether. The clear solution is added to 100 ml of one of the following solvent mixtures, and an amount of 200 mg of glacial acetic acid is then added to the obtained solvent liquor.

As described in Example 66, a sample of 10 g of wool flannel is treated in each case in the respective solvent liquor.

| Example No. | Solvent mixture | Per cent by vol. |
|---|---|---|
| 67 | perchloroethylene/methanol | 95:5 |
| 68 | perchloroethylene/ethanol | 90:10 |
| 69 | perchloroethylene/ethyleneglycol monomethyl ether | 95:5 |
| 70 | perchloroethylene/ethyleneglycol monoethyl ether | 95:5 |
| 71 | perchloroethylene/dimethylformamide | 95:5 |

Table IV

| Ex. No. | (analytical test) Content of anti-insect agent in per cent by weight of the wool. | |
|---|---|---|
| | original | after two drycleanings |
| 66 | 0.25 % | 0.06 % |
| 67 | 0.95 % | 0.92 % |
| 68 | 1.01 % | 0.92 % |
| 69 | 0.89 % | 0.88 % |
| 70 | 0.86 % | 0.67 % |
| 71 | 0.86 % | 0.86 % |

Table V

| | (biological test) | | | | | |
|---|---|---|---|---|---|---|
| | Moths | | Attagenus | | Anthrenus | |
| Ex. No. | original | cleaned twice | original | cleaned twice | original | cleaned twice |
| 66 | o | x | x | x | o | x |
| 67 | o | o | o | o | o | o |
| 68 | o | o | o | o | o | o |
| 69 | o | o | o | o | o | o |
| 70 | o | o | o | o | o | o |
| 71 | o | o | o | o | o | o | o = moth- or beetleproof
x = not moth- or beetleproof

It is hence clear from Tables IV and V that the employment of a solvent mixture according to the present invention, instead of the use of perchloroethylene alone, appreciably increases the degree of fixing of the anti-insect agent on the wool flannel material.

EXAMPLES 72 TO 74

In Examples 72 to 74, the degree of fixing of the anti-insect agent on keratin-containing material applied from treatment liquors or various composition is evaluated and compared.

EXAMPLE 72

An amount of 200 mg of the anti-insect agent according to Example 1 is dissolved in 2 ml of ethylene glycol monoethyl ether; together with 400 mg of glacial acetic acid the above solution is then added to 200 ml of perchloroethylene (ratio of goods to liquor = 1:10).

A sample of 20 g of wool flannel is treated in this liquor at 45° for 30 minutes, with thorough agitation of the liquor. The material is afterwards squeezed out, and dried at 70°.

The wool sample is subsequently examined to determine the content of anti-insect agent (Table VI).

EXAMPLES 73 AND 74

The process described in Example 72 is repeated, the 200 ml of perchloroethylene being replaced, however, by one of the following solvent mixtures:

| Example No. | Solvent mixture | Per cent by vol. |
|---|---|---|
| 73 | monochlorobenzene/methanol | 95:5 |
| 74 | xylene/methanol | 95:5 |

Table VI

| Ex. No. | Content of anti-insect agent in per cent by weight of the wool. | |
|---|---|---|
| | original | after two drycleanings |
| 72 | 0.2 % | (not determinable) |
| 73 | 0.69 % | 0.51 % |
| 74 | 0.94 % | 0.71 % |

By virtue of the analytically determined amounts of anti-insect agent on the wool material according to Examples 73 and 74, an adequate degree of insect-proofing may be expected, whereas in Example 72, in consequence of the use of only one solvent, this is not the case.

EXAMPLE 75

An amount of 200 mg of the anti-insect agent of the formula

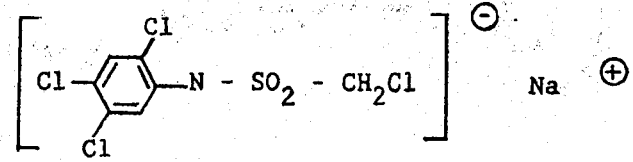

is added to pure perchloroethylene in the one case, and in the other case to a solvent mixture of 96 per cent by volume of perchloroethylene and 4 per cent by volume of methanol. The product dissolves in the liquors with stirring. A sample of 20 g of wool flannel is treated in the one solution and a similar sample in the other, in a vibrating apparatus, the ratio of goods to liquor being in each case 1:10, the treatment temperature 25°, and the duration 20 minutes. The flannel is afterwards centrifuged, and dried at 60°.

The biological examination of the wool samples with respect to proofing against damage from moths and beetles, gave the following results:

| Treatment | Moths | | Attagenus | | Anthrenus | |
|---|---|---|---|---|---|---|
| | original | twice dry-cleaned | original | twice dry-cleaned | original | twice dry-cleaned |
| in perchloroethylene only | oo | o | x | x | x | x |
| in perchloroethylene / methanol (96/4 per cent by volume) | oo | oo | oo | oo | oo | oo |

Evaluation:
oo = very good moth- and beetleproofing
o = adequate moth- and beetleproofing
x = no moth- or beetleproofing.

It can be seen that it is only the wool flannel samples which were finished in the solvent mixture which have adequate moth- and beetleproofing, both in the case of the original and in the case of the samples drycleaned twice.

EXAMPLE 76

A sample of 100 g of wool tricot is cleaned in perchloroethylene without any additives, in a minidrycleaning machine, in the usual manner, and afterwards briefly centrifuged, in order to remove the surplus liquor. After centrifuging, the wool has retained a content of perchloroethylene of 165 g. As the material is tumbled it is sprayed with a solution of 1.5 g of the insecticide salt given in Example 2 in 30 ml of methanol. After spraying, which takes about 5 minutes, the wool material is tumbled for a further 10 minutes. The tricot sample is afterwards dried at 70° with warm air.

The wool material treated in this manner proves to be excellently mothproofed, this applying both to the original and to the sample after further drycleaning.

We claim:
1. A process for imparting a permanent insect proof finish to natural keratin-containing material, comprising the step of applying to the keratin-containing material a solution of 0.1 to 5 per cent by weight, relative to said keratin-containing material, of at least one salt of a stomach poison insecticide, said salt consisting of a compound of the formula:

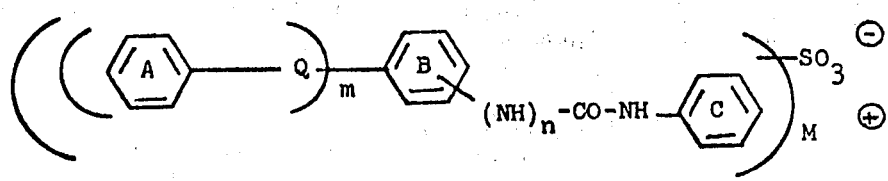

wherein ring A is substituted by one or two chlorine or bromine atoms, or by a chlorine atom and a methyl group,
ring B is substituted by a chlorine or bromine atom and/or by a trifluormethyl group,
ring C is substituted by one to three chlorine or bromine atoms, or by one to two trifluoromethyl groups, or by a chlorine atom and a trifluoromethyl group, or by a chlorine atom and a p-chlorophenoxy group,
Q is a direct bond or an oxygen or a sulfur bridge,
m and n each independently represent 0 or 1, and
M+ is an inorganic or organic cation, in a mixed solvent consisting essentially of
a. 80 to 99% by weight of trichloroethylene, 1,1,1-trichloroethane, tetrachloroethylene or trifluorotrichloroethane, and
b. 20 to 1% by weight of methanol, ethyleneglycol monomethyl ether, or dimethylformamide.
2. The process of claim 1, wherein M+ is a metal cation and/or an ammonium ion.
3. The process of claim 1, wherein M+ is an alkali metal cation or an ammonium ion.
4. The process of claim 1, wherein M+ is an S-alkylisothiourea cation.
5. The process of claim 1, wherein the salt of the insecticide is of the formula:

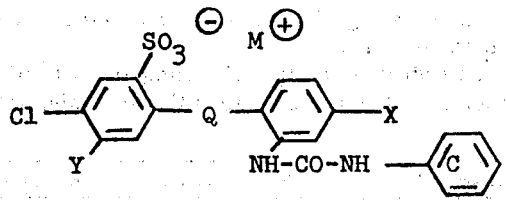

wherein ring
C is substituted by one to two chlorine atoms, or by one to two trifluoromethyl groups, or by a chlorine atom and a trifluoromethyl group,
Q is an oxygen or a sulfur bridge,
X is a chlorine atom or a trifluoromethyl group, and
Y is hydrogen or a chlorine atom.
6. The process of claim 1, wherein the solution is applied to the keratin-containing material in an amount containing 0.1 to 2% of the salt of the insecticide, relative to the weight of the keratin-containing material.
7. The process of claim 1, wherein the solution is applied to the natural keratin-containing material by an exhaust process.
8. The process of claim 1, wherein the solution is applied to the natural keratin-containing material by spraying.
9. The process of claim 1, wherein the solution further contains 0.5 to 4% of a lower aliphatic or aromatic carboxylic acid, relative to the weight of the keratin-containing material.

10. The process of claim 9, wherein the mixed solvent consists essentially of 90 to 99% of solvent (a) and 10 to 1% of solvent (b), and the solution further contains 0.5 to 4% of an aliphatic carboxylic acid, relative to the weight of the keratin-containing material.

11. The process of claim 9, wherein the solution further contains acetic acid.

12. The process of claim 1, wherein the natural keratin-containing material is hair or feathers.

13. The process of claim 12, wherein the natural keratin-containing material is wool.

14. The natural, keratin-containing material permanently finished by the process of claim 1.

UNITED STATES PATENT AND TRADEMARK OFFICE
CERTIFICATE OF CORRECTION

PATENT NO. : 3,968,298
DATED : July 6, 1976
INVENTOR(S) : GERHARD REINERT ET AL

It is certified that error appears in the above-identified patent and that said Letters Patent are hereby corrected as shown below:

Column 29, claim 11, line 9, change "9" to -- 10 --, further in line 9, change "solution" to -- acid --; and in column 30, line 1, change "further contains" to -- is --.

Signed and Sealed this

Twenty-first Day of September 1976

[SEAL]

Attest:

RUTH C. MASON
*Attesting Officer*

C. MARSHALL DANN
*Commissioner of Patents and Trademarks*